US008366791B1

(12) United States Patent  
Warner et al.

(10) Patent No.: US 8,366,791 B1
(45) Date of Patent: Feb. 5, 2013

(54) FORMULATION AND METHOD FOR HAIR DYEING

(75) Inventors: John C. Warner, Wilmington, MA (US); Michael S. Viola, Burlington, MA (US)

(73) Assignee: Warner Babcock Institute, Wilmington, MA (US)

( * ) Notice: Subject to any disclaimer, the term of this patent is extended or adjusted under 35 U.S.C. 154(b) by 0 days.

(21) Appl. No.: 13/225,145

(22) Filed: Sep. 2, 2011

(51) Int. Cl.
*A61Q 5/10* (2006.01)

(52) U.S. Cl. ............. 8/405; 8/406; 8/412; 8/424; 8/431; 8/435

(58) Field of Classification Search .............. 8/405, 406, 8/412, 424, 431, 435
See application file for complete search history.

(56) References Cited

U.S. PATENT DOCUMENTS

| | | | |
|---|---|---|---|
| 3,861,868 A | 1/1975 | Milbrada | |
| 3,884,627 A | 5/1975 | Brody | |
| 3,970,423 A | 7/1976 | Brody | |
| 3,993,436 A | 11/1976 | Fujinuma | |
| 4,212,645 A | 7/1980 | Leon | |
| 4,746,322 A | 5/1988 | Herlihy | |
| 4,806,360 A | 2/1989 | Leong | |
| 4,855,144 A | 8/1989 | Leong | |
| 4,904,274 A * | 2/1990 | Schultz et al. ................. | 8/406 |
| 5,032,138 A | 7/1991 | Wolfram | |
| 5,131,912 A | 7/1992 | Ehara | |
| 5,603,734 A | 2/1997 | Prota | |
| 6,004,355 A | 12/1999 | Dias | |
| 6,022,381 A | 2/2000 | Dias | |
| 6,309,426 B1 | 10/2001 | Dias | |
| 6,398,821 B1 | 6/2002 | Dias | |
| 6,432,147 B1 | 8/2002 | Dias | |
| 6,669,933 B2 | 12/2003 | Duffer | |
| 6,743,264 B2 | 6/2004 | Sarojini | |
| 7,066,968 B2 | 6/2006 | Chan | |
| 7,226,487 B2 | 6/2007 | Lim | |
| 7,232,466 B2 | 6/2007 | Narasimhan | |
| 7,303,592 B2 | 12/2007 | Lim | |
| 7,851,501 B2 | 12/2010 | Aydt | |
| 2002/0032933 A1 | 3/2002 | Dias | |
| 2002/0053110 A1 | 5/2002 | Dias | |
| 2003/0028979 A1 | 2/2003 | Duffer | |
| 2003/0154562 A1 | 8/2003 | Sarojini | |
| 2005/0005370 A1 | 1/2005 | Lim | |
| 2011/0113570 A1 | 5/2011 | Warner | |
| 2011/0113571 A1 | 5/2011 | Warner | |
| 2011/0113573 A1 | 5/2011 | Warner | |
| 2011/0271465 A1 | 11/2011 | Yamaguchi | |

FOREIGN PATENT DOCUMENTS

| | | |
|---|---|---|
| WO | 9827941 A1 | 7/1998 |
| WO | 9827942 A1 | 7/1998 |
| WO | 9827943 A1 | 7/1998 |
| WO | 9827944 A1 | 7/1998 |
| WO | 9827945 A1 | 7/1998 |

OTHER PUBLICATIONS

STIC Search Report dated Oct. 25, 2011.*

* cited by examiner

*Primary Examiner* — Eisa Elhilo
(74) *Attorney, Agent, or Firm* — The Patent Practice of Szmanda & Shelnut, LLC

(57) ABSTRACT

Disclosed and claimed herein are a natural coloring formulation for coloring hair, and methods of its use. The coloring formulation includes a catechol-based precursor and an oxidizing agent. Additionally an alkalizing agent may be present. The formulation is substantially free of organic solvents, co-solvents and diluents.

29 Claims, No Drawings

FORMULATION AND METHOD FOR HAIR DYEING

FIELD OF THE INVENTION

The present invention is in the field of compositions and methods for dyeing hair.

BACKGROUND

Materials have been dyed and colored for thousands of years. While natural substances have historically been used to color most materials, these substances are often unable to permanently dye many types of materials. There is, therefore, a large demand for synthetic dye formulations that permanently color a material, including natural and artificial fibers, among many other beneficial uses. One of the largest markets for permanent dye formulations is the hair coloring market.

Most permanent hair color products contain a developer and an alkalizing agent. The developer is usually an oxidizing agent such as hydrogen peroxide in water or a cream lotion, and the alkalizing agent is most often ammonia or ammonia substitutes such as organic amines. Alkalizing agents cause the hair to swell and thus allow the pigment to penetrate the hair cuticle deep enough to reach and replace the natural melanin.

Several studies have suggested that the chemicals found in synthetic hair dyes, including ammonia, organic bases such as amines, lead, organic solvents and coal tar derivatives, are either toxic or can have undesirable side-effects such as hair loss, burning, redness, itchy skin, swelling, or breathing trouble. Moreover, most hair dye formulations employ oxidizing agents in high concentration. As a result, many people decide to forego hair dyes to avoid exposure to the chemicals found in the coloring compositions.

Although there are some natural formulations that employ compounds found in nature, they tend to be inconsistent and, often, provide only temporary results.

As a result, there is a continued need for coloring compositions that use natural compounds rather than synthetic chemicals to color hair permanently. Additionally, there is a continued demand for efficient and environmentally-friendly formulations and methods for coloring hair either permanently or semi-permanently that do not involve the use of organic solvents or organic bases. Further, there is a continued demand for hair dye formulations that use oxidizing agents in lower concentration.

Most formulations for dying hair are made to produce a color specific to a given chemical colorant. However, in managing the target grey hair, it is frequently desired to reproduce the original natural color of the hair rather than to impart a new color. There is thus a continuing demand for hair coloring products that reproduce as closely as possible the original natural color of the hair.

Without intending to be bound by theory, possible components of natural coloring compositions are natural and/or organic molecules that form non-covalent interactions with color polymers. While traditional methods of synthesis use synthetic chemicals such as solvents to form chemical products, non-covalent derivitization ("NCD") uses the natural non-covalent intermolecular interactions between a directing material and a target compound to modify the properties of the target compound. When the directing material and the target compound interact, the resulting derivative possesses properties that can be significantly different from either the target compound or the directing material alone. Often, the properties of the derivative can be modified by altering the ratio of target compound to directing material, and/or changing the directing material. Another benefit of the NCD method is that the directing material and the target compound are typically both incorporated into the product, thereby eliminating at least some waste during production.

DETAILED DESCRIPTION

In a first embodiment, the instant application for patent discloses and claims a formulation for dying hair comprising a catechol-based dye precursor or a pharmaceutically acceptable salt thereof, an oxidizing agent and water, wherein the formulation for dying hair is substantially free of organic solvents, co-solvents and diluents.

In a second embodiment, the instant application for patent discloses and claims process for dying hair comprising providing a first admixture comprising a catechol-based dye precursor or a pharmaceutically acceptable salt thereof and providing a second admixture comprising an oxidizing agent, wherein the first admixture and second admixture are substantially free of organic solvents, co-solvents and diluents.

In a third embodiment, the instant application for patent discloses and claims a process for dying hair comprising providing a first admixture comprising a catechol-based dye precursor or a pharmaceutically acceptable salt thereof and providing one or more oxidizing agents, wherein the first admixture and one or more oxidizing agents are substantially free of organic solvents, co-solvents and diluents.

In the above embodiments, the catechol-based precursors can be the unsubstituted catechol compounds or they can have one or both of their phenolic hydroxy groups esterified to form pharmaceutically acceptable esters. The term catechol-based precursor is intended to mean either or both of the esterified or unesterified compound or compounds.

In the above embodiments, the first admixture comprising a catechol-based dye precursor can further comprise bicarbonate and/or carbonate salts.

In the above embodiments, the catechol-based dye precursor is chosen from L-DOPA, D-DOPA or pharmaceutically acceptable salts thereof and/or esters thereof or mixtures thereof.

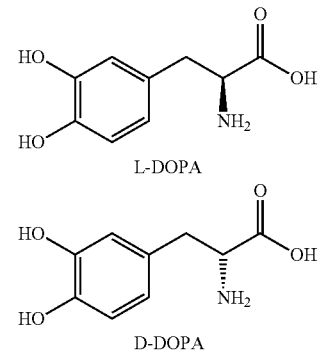

L-DOPA

D-DOPA

In the above embodiments, the catechol-based dye precursor is of the formula

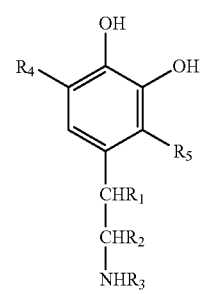

wherein $R_1$ and $R_2$ can be the same or different and are: H, alkyl or 1-4C, $NH_2$, OH, COOR' wherein R' is alkyl of 1-4C or H, $CONH_2$, halogen, OR" wherein R" is alkyl of 1-4C, $CH_2OH$, $CH_2NH_2$, CONR'R" wherein R' and R" can be the same or different; $R_3$ is H or alkyl of 1-4C or COR"; $R_4$, $R_5$ can be the same or different and are: H, alkyl of 1-4C, $NH_2$, OH, COOH, $CONH_2$, halogen, OR", $NO_2$, $SO_3$, HNR" or NR"R". Further, the catechol-based dye precursor can be any pharmaceutically acceptable salt of the above compounds, any pharmaceutically acceptable ester of the above compounds or a mixture thereof.

In the above embodiments, $R_1$ and $R_2$, denoted supra may be non hydrogen substituents, and the catechol-based dye precursor comprises two or more diastereomers.

In the above embodiments, the oxidizing agent can be chosen from sodium periodate, potassium periodate, ammonium periodate or mixtures thereof.

In the above embodiments, the oxidizing agent can be a pharmaceutically acceptable salt whose anion is chosen from periodate, persulfate, perborate, iodate, peroxydisulfate, monopersulfate, or hypochlorite. In addition, other oxidizing agents can be used. These include (2,2,6,6-tetramethylpiperidin-1-yl)oxyl (TEMPO), ferric chloride, tert-butyl hydroperoxide, benzoyl peroxide and cerium (IV) ammonium nitrate.

The above embodiments can comprise a pharmaceutically acceptable carbonate salt and a pharmaceutically acceptable bicarbonate salt in a mole ratio of from about 0.05 to about 20. In a further embodiment the mole ratio can be about 0.5 to about 2.0. In a further embodiment, the mole ratio can be about 0.75 to about 1.5.

The admixtures and materials used in the above embodiments can further be substantially free of organic bases and/or substantially free of ammonia.

In the above embodiments, the mole ratio of the oxidizing agent to the catechol-based dye precursor may be, for example, greater than about 0.01 and less than about 2.0. Further, the mole ratio of the oxidizing agent to the catechol-based dye precursor may be, for example, between about 0.1 to about 1.0. Still further, the mole ratio of the oxidizing agent to the catechol-based dye precursor may be, for example, between about 0.2 to about 0.5.

In the second embodiment, the process for dying hair may further comprise mixing the first admixture and second admixture prior to treating the hair.

In the second embodiment, the process for dying hair may further comprise applying the first admixture to the hair, and applying the second admixture to the hair.

In the third embodiment, the process for dying hair may further comprise mixing the first admixture and the one or more oxidizing agents prior to treating the hair. The above process can further comprise diluting the one or more oxidizing agents with water prior to mixing with the first admixture.

In the third embodiment, the process for dying hair may further comprise applying the first admixture to the hair, diluting the one or more oxidizing agents with water and applying the diluted one or more oxidizing agents to the hair.

Herein, the conjunction "or" is not intended to be exclusive unless otherwise noted. For example, the phrase "or alternatively" is intended to be exclusive. Further, when used in connection with chemical substitution at a specific position, the conjunction "or" is intended to be exclusive. As used herein, the adjective "exemplary" is used simply to point to an example and is not meant to indicate preference.

By the term "pharmaceutically acceptable salt" is intended salts with pharmaceutically acceptable acids or bases. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the catechol-based precursor, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Pharmaceutically acceptable salts of carboxylates and other oxo-acids can be formed with cationic species such as alkali or alkaline earth metal ions including sodium, lithium, potassium, calcium, magnesium, and the like. Further, pharmaceutically acceptable salts include, when appropriate, nontoxic ammonium, quaternary ammonium, and amine cations as well as natural product cations such as choline and acetyl choline and the like. Anionic counterions include halides, hydroxide, carboxylate, sulfate, phosphate, nitrate, alkyl (having from 1 to 6 carbon atoms) sulfonate and aryl sulfonate.

Without intending to be bound by theory, it is believed that esters of the catechol-based precursors of this invention can be used to slow the oxidation of the catechol-based precursor to allow sufficient time for diffusion into the hair cuticle. As used herein, the term "pharmaceutically acceptable ester" refers to esters which hydrolyze readily in situ and include those that break down readily within in the hair to leave the catechol-based precursor or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety has not more than 6 carbon atoms. Examples of particular esters include, but are not limited to, formates, acetates, propionates, butyrates, citrates, benzoates, lactates, acrylates and ethylsuccinates.

Oxidizers may be uncoated or may be coated with materials suitable for controlled release prepared by known techniques, including microencapsulation, to delay adsorption of the dye or dye intermediates into the hair and thereby provide a sustained action over a longer period of time. For example, a material such as glyceryl monostearate or glyceryl distearate alone or with a wax may be employed as a material suitable for controlled release.

As further examples, an oligomer/polymer of hydroxyacetic acid and lactic acid or a oligomer/polymer of lactic acid and glycolic acid are suitable for use as an encapsulant material for controlled release of the oxidizing agent and can be used in conjunction with nonionic, cationic, anionic and zwitterionic surfactants from a melt or from admixture to produce the encapsulated oxidizing agent.

Encapsulated and microencapsulated oxidizing agents can be prepared by techniques known in the art; which techniques include, for example, pan coating, air suspension coating, centrifugal extrusion, core-shell encapsulation using a vibrational nozzle, spray drying, ionotropic gelation, coacervation, interfacial polycondensation, interfacial crosslinking, in-situ polymerization or matrix polymerization.

Organic compounds such as the catechol-based precursor, described supra, may be synthesized in various solvents, co-solvents and diluents and under various conditions. Accordingly, there may be residual solvents, co-solvents and diluents present as contaminants. Herein, the term "substantially free of" in reference to solvents, co-solvents and diluents, is intended to mean less than about 5% w/w of the admixture containing the catechol-based precursor. As used herein, a solvent is understood to be a material that forms a solution with a solid or liquid solute. As used herein, a co-solvent is understood to be a material that, in conjunction with a solvent or another co-solvent, forms a solution with a solid or liquid solute. As used herein, a diluent is understood to be a filler, thinner or dispersing agent, used alone or in conjunction with a solvent and/or co-solvent.

Organic compounds such as the catechol-based precursor, described supra, may be synthesized using various organic bases such as amines, pyridine and its derivatives, imidazole and its derivatives and the like and under various conditions. Accordingly, there may be residual organic bases present as contaminants. Herein, the term "substantially free of" in reference to organic bases is intended to mean less than about 5% w/w of the admixture containing the catechol-based precursor.

The hair dye may be supplied in kit form and may comprise a formulation having the catechol-based precursor, and the oxidizing agent in the same or separate containers. Moreover, the kits may provide sufficient materials for a single application or multiple applications. Concentrations may vary depending on the specific application contemplated. In one example, whether in separate solutions or in one solution, the total molal concentration of the catechol-based precursor or its pharmaceutically acceptable ester or salt in water may be 0.01-2.0 mol/kg. In a further example, whether in separate solutions or in one solution, the total molal concentration of the catechol-based precursor or its pharmaceutically acceptable ester or salt in water may be 0.1-1.0 mol/kg. In a further example, whether in separate solutions or in one solution, the total molal concentration of the catechol-based precursor or its pharmaceutically acceptable ester or salt in water may be 0.15-0.5 mol/kg. In one example, whether in separate solutions or in one solution, the total molal concentration of the oxidizing agent in water may be 0.005-0.2 mol/kg. In a further example, whether in separate solutions or in one solution, the total molal concentration of the oxidizing agent in water may be 0.01-0.2 mol/kg. In a further example, whether in separate solutions or in one solution, the total molal concentration of the oxidizing agent in water may be 0.025-0.1 mol/kg.

Notwithstanding the foregoing, an exemplary mole ratio of the oxidizing agent to the catechol-based dye precursor is greater than about 0.01 and less than about 2.0. In a further example, the mole ratio of the oxidizing agent to the catechol-based dye precursor is between about 0.1 to about 1.0. In a still further example, the mole ratio of the oxidizing agent to the catechol-based dye precursor is between about 0.2 to about 0.5.

Further, in one example, the first admixture can comprise a pharmaceutically acceptable carbonate salt and a pharmaceutically acceptable bicarbonate salt in a mole ratio of from about 0.05 to about 20. In a further example, the mole ratio can be about 0.5 to about 2.0. In a further example, the mole ratio can be about 0.75 to about 1.5, wherein the bicarbonate is present at a molal concentration in water of 0.2-2 mol/kg.

EXAMPLES

Materials used in these examples were obtained from Aldrich Chemical Co. unless otherwise indicated. Percentages are wt/wt unless otherwise noted.

Example 1

Into a vial are added 0.25 g (1.27 mmol) of L-DOPA, 0.26 g (3.1 mmol) of sodium bicarbonate, and 0.054 g (0.25 mmol) of sodium periodate. 5 mL of deionized water are added and the materials rapidly mixed. The admixture turns dark brown/black immediately in the vial. The admixture was applied to a subject's hair using a small brush. The admixture was massaged into the subjects hair using gloved fingers. The admixture was remade and applied as before, two more rimes. A plastic washing cap was placed over the subjects head surrounding the treated hair and the subjects head was covered by a standard hair drier whose temperature was set at "perm" or 54° C. After 12 minutes, the hair drier and the washing cap were removed. The previously described admixture was remade and applied to the subject's hair as previously described. A total of three applications were made with the final heating step being 20 minutes in length. The hair was then rinsed with room temperature tap water for 5 min. The hair was then shampooed with standard shampoo and dried. Unexpectedly the white hair of a subject whose original natural color was brown, became brown, closely resembling the subject's original brown color; and the white hair of a subject whose original natural color was black, became black, again closely resembling the subject's original black color. Moreover, unexpectedly the above results were achieved in the absence of ammonia or organic amines and peroxides.

Examples 2-7

For each of Examples 2-7, two solutions were prepared as indicated in Table 1, infra. A swatch of grey hair weighing 0.5 grams, tied at one end was used for each experiment. For each experiment, mixture #1 and #2 were rapidly blended together by shaking. Using an eyedropper, a 1 ml aliquot of the mixture was then applied to the hair and massaged through it for 10 seconds. The treated hair sample was then wrapped in aluminum foil and suspended from a hair dryer at the set temperature. After the designated time, the sample was removed and then rinsed with warm tap water. The hair sample was allowed to dry at room temperature. All the hair samples were then rank ordered among each other and assigned a numerical value for lightness/darkness with 1 being barely dyed and 10 being the darkest.

Examples 8-19

As in Examples 2-7, but to each of the two solutions was added the indicated amount of a 1% aqueous solution of sodium alginate (available from Sigma Chemical Co). Hair samples were evaluated as above.

Example 20

The following synthetic method can be used to make the oligomer/polymer of hydroxyacetic acid and lactic acid, described supra, suitable for use as a matrix for encapsulating the oxidizing agent: 300 grams (3.95 moles) of hydroxyacetic acid and 336 grams (3.73 moles) of lactic acid are mixed and heated to 190° C. to condense the acids and eliminate water. After heating the mixture for a period of three hours at 190° C. and atmospheric pressure, the pressure is reduced to 5 mm of mercury and heating is continued for another 2 hours at 210° C.

The present invention has been described in connection with various embodiments. Notwithstanding the foregoing, it should be understood that modifications, alterations, and additions can be made to the invention without departing from the scope of the invention as defined by the appended claims.

TABLE 1

| | Mixture #1 | | | | Mixture #2 | | | | | Hair | Score: |
|---|---|---|---|---|---|---|---|---|---|---|---|
| Exper- | L-DOPA | | Sodium Bicarbonate | | Water, | Sodium Periodate | | Water, | Temp., | Periodate/DOPA | Treatment | 1 = Light |
| iment | g | mmol | g | mmol | g | g | mmol | g | °C. | Mole Ratio | Time, min | 10 = Dark |
| 2 | 0.01 | 0.051 | 0 | 0.000 | 0.99 | 0.005 | 0.023 | 0.995 | 20 | 0.461 | 20 | 1 |
| 3 | 0.055 | 0.279 | 0.104 | 1.238 | 0.841 | 0.04 | 0.187 | 0.96 | 20 | 0.670 | 20 | 5 |
| 4 | 0.1 | 0.507 | 0.052 | 0.619 | 0.848 | 0.005 | 0.023 | 0.995 | 20 | 0.046 | 40 | 5 |
| 5 | 0.01 | 0.051 | 0 | 0.000 | 0.99 | 0.0225 | 0.105 | 0.9775 | 55 | 2.074 | 40 | 4 |
| 6 | 0.055 | 0.279 | 0.104 | 1.238 | 0.841 | 0.0225 | 0.105 | 0.9775 | 55 | 0.377 | 30 | 10 |
| 7 | 0.1 | 0.507 | 0.052 | 0.619 | 0.848 | 0.04 | 0.187 | 0.96 | 55 | 0.369 | 30 | 10 |

TABLE 2

| | Mixture #1 | | | | | Mixture #2 | | | (Both Sol'ns.) | | | | Score: |
|---|---|---|---|---|---|---|---|---|---|---|---|---|---|
| Exper- | L-DOPA | | Sodium Bicarbonate | | | Sodium Periodate | | | Periodate/ DOPA | 1% Sodium Alginate | Temp., | Time, | 1=Light |
| iment | g | mmol | g | mmol | Water | g | mmol | Water | Mole Ratio | Polymer | °C. | min | 10=Dark |
| 8 | 0.01 | 0.051 | 0.052 | 0.619 | 0.663 | 0.0225 | 0.105 | 0.7025 | 2.074 | 0.275 | 20 | 30 | 4 |
| 9 | 0.01 | 0.051 | 0.104 | 1.238 | 0.336 | 0.04 | 0.187 | 0.41 | 3.688 | 0.55 | 20 | 40 | 2 |
| 10 | 0.055 | 0.279 | 0 | 0.000 | 0.67 | 0.005 | 0.023 | 0.72 | 0.084 | 0.275 | 20 | 30 | 1.5 |
| 11 | 0.055 | 0.279 | 0.052 | 0.619 | 0.343 | 0.0225 | 0.105 | 0.4275 | 0.377 | 0.55 | 20 | 40 | 8 |
| 12 | 0.1 | 0.507 | 0.104 | 1.238 | 0.521 | 0.0225 | 0.105 | 0.7025 | 0.207 | 0.275 | 20 | 20 | 6 |
| 13 | 0.1 | 0.507 | 0 | 0.000 | 0.35 | 0.04 | 0.187 | 0.41 | 0.369 | 0.55 | 20 | 30 | 5 |
| 14 | 0.01 | 0.051 | 0.104 | 1.238 | 0.336 | 0.005 | 0.023 | 0.445 | 0.461 | 0.55 | 55 | 30 | 5 |
| 15 | 0.01 | 0.051 | 0.052 | 0.619 | 0.663 | 0.04 | 0.187 | 0.685 | 3.688 | 0.275 | 55 | 20 | 1.5 |
| 16 | 0.055 | 0.279 | 0.052 | 0.619 | 0.343 | 0.005 | 0.023 | 0.445 | 0.084 | 0.55 | 55 | 20 | 3 |
| 17 | 0.055 | 0.279 | 0 | 0.000 | 0.67 | 0.04 | 0.187 | 0.685 | 0.670 | 0.275 | 55 | 40 | 9 |
| 18 | 0.1 | 0.507 | 0.104 | 1.238 | 0.521 | 0.005 | 0.023 | 0.72 | 0.046 | 0.275 | 55 | 40 | 7 |
| 19 | 0.1 | 0.507 | 0 | 0.000 | 0.35 | 0.0225 | 0.105 | 0.4275 | 0.207 | 0.55 | 55 | 20 | 8 |

We claim:

1. A formulation for dying hair, comprising:
   a. a catechol-based dye precursor;
   b. an oxidizing agent; and
   c. water;
   wherein the formulation for dying hair is substantially free of organic solvents, co-solvents and diluents, and wherein the catechol-based dye precursor is of the formula

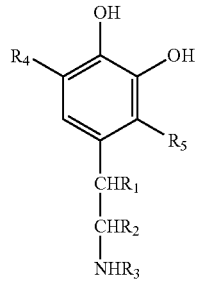

wherein $R_1$ and $R_2$ can be the same or different and are: H, alkyl of 1-4C, $NH_2$, OH, COOR', $CONH_2$, halogen, OR", $CH_2OH$, $CH_2NH_2$, CONR'R" wherein R' and R" can be the same or different, wherein R' is alkyl of 1-4C or H, wherein R" is alkyl of 1-4C; $R_3$ is H or alkyl of 1-4C or COR"; $R_4$, $R_5$ can be the same or different and are: H, alkyl of 1-4C, $NH_2$, OH, COOH, $CONH_2$, halogen, OR", $NO_2$, $SO_3R'$, HNR", or NR"R" or any pharmaceutically acceptable salts thereof or mixtures thereof, and wherein when R3 is H or alkyl, R1 is alkyl of 1-4C, $NH_2$, COOR', $CONH_2$, halogen, OR", $CH_2OH$, $CH_2NH_2$, CONR'R" wherein R' and R" can be the same or different, wherein R' is alkyl of 1-4C or H, wherein R" is alkyl of 1-4C.

2. The formulation for dying hair of claim 1, wherein $R_1$ and $R_2$ are non hydrogen substituents and the catechol-based dye precursor comprises two or more diastereomers.

3. The formulation for dying hair of claim 1, wherein the formulation for dying hair is substantially free of organic bases.

4. The formulation for dying hair of claim 3, further comprising a pharmaceutically acceptable bicarbonate salt.

5. The formulation for dying hair of claim 4, wherein the oxidizing agent is chosen from sodium periodate, potassium periodate, ammonium periodate or mixtures thereof.

6. The formulation for dying hair of claim 5, wherein the mole ratio of the oxidizing agent to the catechol-based dye precursor is greater than about 0.01 and less than about 2.0.

7. The formulation for dying hair of claim 6, wherein the oxidizing agent is a pharmaceutically acceptable salt whose anion is chosen from periodate, persulfate, perborate, iodate peroxydisulfate, monopersulfate, or hypochlorite or mixtures thereof.

8. The formulation for dying hair of claim 6, wherein the oxidizing agent is chosen from ferric chloride, tert-butyl hydroperoxide, benzoyl peroxide, cerium (IV) ammonium nitrate or (2,2,6,6-tetramethylpiperidin-1-yl)oxyl (TEMPO) or mixtures thereof.

9. A process for dying hair, comprising:
   a. providing a first admixture comprising a catechol-based dye precursor or a pharmaceutically acceptable salt thereof; and
   b. providing a second admixture comprising an oxidizing agent;

wherein the first admixture and second admixture are substantially free of organic solvents, co-solvents and diluents, and wherein the hair to be dyed is un-pretreated.

10. The process of claim 9, further comprising mixing the first admixture and second admixture prior to treating hair.

11. The process of claim 9, further comprising applying the first admixture to the hair, and applying the second admixture to the hair.

12. The formulation for dying hair of any of claim 10 or 11, wherein the catechol-based dye precursor is of the formula

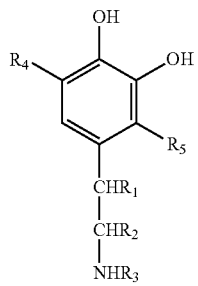

wherein $R_1$ and $R_2$ can be the same or different and are: H, alkyl of 1-4C, $NH_2$, OH, COOR', $CONH_2$, halogen, OR", $CH_2OH$, $CH_2NH_2$, CONR'R" wherein R' and R" can be the same or different, wherein R' is alkyl of 1-4C or H, wherein R" is alkyl of 1-4C; $R_3$ is H or alkyl of 1-4C or COR"; $R_4$, $R_5$ can be the same or different and are: H, alkyl of 1-4C, $NH_2$, OH, COOH, $CONH_2$, halogen, OR", $NO_2$, $SO_3R'$, HNR", or NR"R" or any pharmaceutically acceptable salts thereof or mixtures thereof.

13. The formulation for dying hair of claim 12, wherein $R_1$ and $R_2$ are non hydrogen substituents and the catechol-based dye precursor comprises two or more diastereomers.

14. The formulation for dying hair of claim 12, wherein the formulation for dying hair is substantially free of organic bases.

15. The formulation for dying hair of claim 12, further comprising a pharmaceutically acceptable bicarbonate salt.

16. The formulation for dying hair of claim 15, wherein the oxidizing agent is chosen from sodium periodate, potassium periodate, ammonium periodate or mixtures thereof.

17. The formulation for dying hair of claim 16, wherein the mole ratio of the oxidizing agent to the catechol-based dye precursor is greater than about 0.01 and less than about 2.0.

18. The formulation for dying hair of claim 17, wherein the oxidizing agent is a pharmaceutically acceptable salt whose anion is chosen from periodate, persulfate, perborate, iodate peroxydisulfate, monopersulfate, or hypochlorite or mixtures thereof.

19. The formulation for dying hair of claim 17, wherein the oxidizing agent is chosen from ferric chloride, tert-butyl hydroperoxide, benzoyl peroxide, cerium (IV) ammonium nitrate or (2,2,6,6-tetramethylpiperidin-1-yl)oxyl (TEMPO) or mixtures thereof.

20. A process for dying hair, comprising:
 a. providing an admixture comprising a catechol-based dye precursor or a pharmaceutically acceptable salt thereof; and
 b. providing one or more oxidizing agents contained in a controlled release matrix;

wherein the first admixture and one or more oxidizing agents are substantially free of organic solvents, co-solvents and diluents.

21. The process of claim 20, wherein the controlled release matrix is a microencapsulation.

22. The process of claim 20, further comprising mixing the admixture and the one or more oxidizing agents contained in a controlled release matrix prior to treating hair.

23. The process of claim 20, further comprising suspending the one or more oxidizing agents contained in a controlled release matrix in water to form a suspension, applying the admixture to the hair and applying the suspension to the hair.

24. The formulation for dying hair of any one of claims 22-23, wherein the catechol-based dye precursor is of the formula

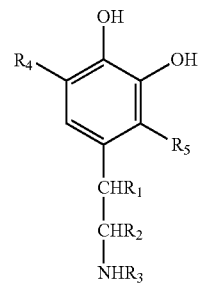

wherein $R_1$ and $R_2$ can be the same or different and are: H, alkyl of 1-4C, $NH_2$, OH, COOR', $CONH_2$, halogen, OR", $CH_2OH$, $CH_2NH_2$, CONR'R" wherein R' and R" can be the same or different, wherein R' is alkyl of 1-4C or H, wherein R" is alkyl of 1-4C; $R_3$ is H or alkyl of 1-4C or COR"; $R_4$, $R_5$ can be the same or different and are: H, alkyl of 1-4C, $NH_2$, OH, COOH, $CONH_2$, halogen, OR", $NO_2$, $SO_3R'$, HNR", or NR"R" or any pharmaceutically acceptable salts thereof or mixtures thereof.

25. The formulation for dying hair of claim 24, wherein $R_1$ and $R_2$ are non hydrogen substituents and the catechol-based dye precursor comprises two or more diastereomers.

26. The process of claim 25, wherein the one or more oxidizing agents are chosen from sodium periodate, potassium periodate, ammonium periodate or mixtures thereof.

27. The process of claim 25, wherein the one or more oxidizing agents are pharmaceutically acceptable salts whose anion is chosen from periodate, persulfate, perborate, ferricyanide, iodate, peroxydisulfate, monopersulfate, or hypochlorite.

28. The process of claim 25, wherein the oxidizing agent is chosen from ferric chloride, tertbutyl hydroperoxide, benzoyl peroxide, cerium (IV) ammonium nitrate or (2,2,6,6-tetramethylpiperidin-1-yl)oxyl (TEMPO) or mixtures thereof.

29. The formulation for dying hair of claim 1, wherein $R_2$ is COOR' wherein R' is alkyl of 1-4C or H, or COR" wherein R" is $NH_2$, NHR', $NR'_2$ and $R_1$ is H, OH, alkyl of 1-4C, $NH_2$, OH, COOR', or COR" wherein R" is $NH_2$, NHR', $NR'_2$, halogen, OR', $CH_2OH$, $CH_2NH_2$, $R_3$ is H or alkyl of 1-4C or COR'; $R_4$, $R_5$ can be the same or different and are: H, alkyl of 1-4C, $NH_2$, OH, COOH, $CONH_2$, halogen, OR', $NO_2$, $SO_3R'$, HNR', or $NR'_2$ or any pharmaceutically acceptable salts thereof or mixtures thereof.

* * * * *